United States Patent
Zanarotti et al.

(10) Patent No.: US 9,402,885 B2
(45) Date of Patent: Aug. 2, 2016

(54) METHOD OF TREATING GERD WITH ALPHA AND BETA GALACTOSIDASES

(71) Applicant: ALFA WASSERMANN S.P.A., Alanno (PE) (IT)

(72) Inventors: Alessandro Zanarotti, Milan (IT); Gabriele Brunetti, Milan (IT); Sergio Cecchetti, Pozzuolo Martesana (IT)

(73) Assignee: ALFA WASSERMANN S.P.A., Alanno (IT)

( * ) Notice: Subject to any disclaimer, the term of this patent is extended or adjusted under 35 U.S.C. 154(b) by 0 days.

(21) Appl. No.: 14/329,869

(22) Filed: Jul. 11, 2014

(65) Prior Publication Data

US 2015/0017149 A1 Jan. 15, 2015

Related U.S. Application Data

(60) Provisional application No. 61/846,571, filed on Jul. 15, 2013.

(51) Int. Cl.
*A61K 38/47* (2006.01)
*A61K 9/00* (2006.01)
*A61K 9/20* (2006.01)

(52) U.S. Cl.
CPC ............... *A61K 38/47* (2013.01); *A61K 9/0056* (2013.01); *A61K 9/2018* (2013.01); *A61K 9/2054* (2013.01); *C12Y 302/01022* (2013.01); *C12Y 302/01023* (2013.01)

(58) Field of Classification Search
None
See application file for complete search history.

(56) References Cited

FOREIGN PATENT DOCUMENTS

| DE | 202006012340 U1 | 9/2007 |
| EP | 0176971 A2 | 9/1985 |
| EP | 2537528 | * 12/2012 |
| EP | 2537528 A1 | 12/2012 |
| WO | 9014101 A1 | 11/1990 |

OTHER PUBLICATIONS

Grossi L. et al. Effect of Alpha Galactosidase on 24 Hour Esophageal pH Profile in Patients with GERD. Gastroenterology 136(5, Suppl 1)A438, May 2009.*
Piche, T. et al. "Modulation by colonic fermentation of LES function in humans" Am. J. Physiol Gastrointest Liver Physiol. Apr. 2000, vol. 278, pp. G578-G584.
Piche, T. et al. "Colonic Fermentation Influences Lower Esophageal Sphincter Function in Gastroesophageal Reflux Disease" Gastroenterology Apr. 2003, vol. 124, No. 4, pp. 894-902.
Grossi, L. et al. "Effect of Alpha-Galactosidase on 24-Hour Esophageal pH Profile in Patients with Gastro-Esophageal Reflux Disease" Abstracts/Digestive and Liver Disease Feb. 2009, vol. 41S, pp. S49.

* cited by examiner

*Primary Examiner* — Ralph Gitomer
(74) *Attorney, Agent, or Firm* — Steinfl & Bruno LLP

(57) ABSTRACT

The present disclosure relates to pharmaceutical or nutritional compositions containing α-galactosidase and β-galactosidase and their use in the prevention and/or treatment of gastroesophageal reflux disease; in particular the present disclosure related to pharmaceutical or nutritional compositions.

4 Claims, No Drawings

METHOD OF TREATING GERD WITH ALPHA AND BETA GALACTOSIDASES

RELATED APPLICATIONS

The present application claims priority to U.S. provisional application Ser. No. 61/846,571 entitled "Pharmaceutical or Nutritional compositions containing Galactosidase and their use" filed on Jul. 15, 2013, which is incorporated herein by reference in its entirety.

The present disclosure may be related to European Application S/N 12172907.3 entitled "Pharmaceutical or nutritional compositions containing galactosidase, and their use" filed on Jun. 21, 2012 and published on Dec. 26, 2012 as EP 2537 528 herein incorporated by reference in its entirety. The present disclosure may also be related to Italian application serial number IT MI20111154 entitled "Composizioni Farmaceutiche o Nutrizionali comprendenti Galattosidasi e loro uso" filed on Jun. 24, 2011 and herein also incorporated by reference in its entirety.

FIELD

The present disclosure relates to pharmaceutical or nutritional compositions containing a galactosidase and their use. In particular the present disclosure relates to pharmaceutical or nutritional compositions useful in the prevention and/or treatment of gastroesophageal reflux disease.

BACKGROUND

Gastroesophageal reflux disease (GERD), gastro-oesophageal reflux disease (GORD), gastric reflux disease, or acid reflux disease is a symptom of mucosal damage caused by stomach acid coming up from the stomach into the esophagus.

GERD is usually caused by changes in the barrier between the stomach and the esophagus, including abnormal relaxation of the lower esophageal sphincter, which normally holds the top of the stomach closed, impaired expulsion of gastric reflux from the esophagus, or a hiatal hernia. These changes may be permanent or temporary. Treatment is typically via lifestyle changes and medications.

As the disorder is so widespread, prevention and/or treatment of gastroesophageal reflux disease is still challenging.

SUMMARY

The present disclosure relates to pharmaceutical or nutritional compositions containing a galactosidase and more particular to compositions comprising α-galactosidase and β-galactosidase and to related methods and systems.

The disclosure also relates to the use of said compositions in the prevention and/or treatment of a gastroesophageal reflux disease and related compositions methods and systems.

Pharmaceutical or nutritional compositions or related methods and systems herein described can be used in nutraceuticals and medical applications in which reduction of acid reflux in an individual is desired and in particular in connection with the treatment and/or prevention of symptoms and conditions such as heartburn regurgitation dyspepsia reflux esophagitis, esophageal strictures, and in additional symptoms and conditions identifiable by a skilled person.

DETAILED DESCRIPTION

The present disclosure relates to pharmaceutical or nutritional compositions comprising a galactosidase as an active ingredient, as well as their use to treat and/or prevent acid reflux in an individual and of a condition associated thereto.

In particular, the present disclosure relates to pharmaceutical or nutritional compositions containing a galactosidase for use in the prevention and/or treatment of gastroesophageal reflux disease (GERD) and/or additional conditions identifiable by a skilled person.

The term "treat" or "treatment" as used herein indicates any activity that is part of a medical care for, or deals with, a condition, medically or surgically. In particular the terms "treating" and "treatment" refer to reduction in severity and/or frequency of symptoms, elimination of symptoms and/or underlying cause, prevention of the occurrence of symptoms and/or their underlying cause, and improvement or remediation of damage. Thus, for example, "treating" a patient involves prevention of a symptom or adverse physiological event in a susceptible individual, as well as modulation and/or amelioration of the status of a clinically symptomatic individual by inhibiting or causing regression of a disorder or disease.

The term "prevention" as used herein with reference to a condition indicates any activity which reduces the burden of mortality or morbidity from the condition in an individual. This takes place at primary, secondary and tertiary prevention levels, wherein: a) primary prevention avoids the development of a disease; b) secondary prevention activities are aimed at early disease treatment, thereby increasing opportunities for interventions to prevent progression of the disease and emergence of symptoms; and/or c) tertiary prevention reduces the negative impact of an already established disease by restoring function and reducing disease-related complications.

The term "condition" as used herein indicates a usually the physical status of the body of an individual, as a whole or of one or more of its parts, that does not conform to a physical status of the individual, as a whole or of one or more of its parts, that is associated with a state of complete physical, mental and possibly social well-being. Conditions herein described include but are not limited disorders and diseases wherein the term "disorder" indicates a condition of the living individual that is associated to a functional abnormality of the body or of any of its parts, and the term "disease" indicates a condition of the living individual that impairs normal functioning of the body or of any of its parts and is typically manifested by distinguishing signs and symptoms. Exemplary conditions include but are not limited to injuries, disabilities, disorders (including mental and physical disorders), syndromes, infections, deviant behaviors of the individual and atypical variations of structure and functions of the body of an individual or parts thereof.

The terms "Gastroesophageal reflux disease" or (GERD), also known as gastro-oesophageal reflux disease (GORD), gastric reflux disease, or acid reflux disease, as used herein indicate a condition that arises when the stomach contents flow back into the oesophagus. In particular, GERDs according to the present disclosure comprise disorders characterized by heartburn and regurgitation, in which in particular, the frequency of the episodes of the otherwise physiological reflux of the stomach contents into the oesophagus increases to the point that the reflux becomes harmful to the oesophageal mucosa and causes the appearance of symptoms and complications, such as oesophagitis and Barrett's oesophagus.

Exemplary GERDs comprise conditions treatable inter alia by suppression of the acid secretion and in particular, via administration of a gastric acid inhibitor such as proton pump inhibitors (PPIs) and/or H2 antihistamines (anti-H2s) and antacids, alone or in combination with dietary adjustments such as reduction of fat administration as well as possibly reduction of lactose administration (Piche et al., 2000; Am J Physiol Gastrointest Liver Physiol 278: G578-84), fructo-oligosaccharides (FOS) administration (Piche et al., Gastroenterology 2003; 124: 894-902) and/or reduction of fermentation in the colon of wholly or partly unabsorbed carbohydrates which may be responsible for the onset or aggravation of gastroesophageal reflux disease.

A preliminary study (9 cases—methodologically elegant and placebo-controlled) has demonstrated that a preparation based on alpha-galactosidase acts as reflux inhibitor (Grossi et al., Digestive and Liver Disease 41S: FISMAD Milan, 28/3-1/4 2009; S49-Abstract). In that study, the administration of alpha-galactosidase for 4 weeks reduced the frequency of Transient Lower Oesophageal Sphincter Relaxations (TLES relaxation), reflux episodes, the percentage of pH<4 and the severity of the reflux symptoms.

In some embodiments of the present disclosure one or more galactosidases can be used in combination with other active ingredients for treatment and/or prevention of a GERD in an individual and/or additional conditions associated to acid reflux such as additional gastroesophageal reflux diseases identifiable by a skilled person.

The term "galactosidase" as used herein indicates a hydrolase enzyme that catalyzes the hydrolysis of galactosides. Exemplary galactosidases in the sense of the disclosure are α-galactosidase and β-galactosidase. The term "α-galactosidase" indicates a glycoside hydrolase enzyme that hydrolyses the terminal alpha-galactosyl moieties from glycolipids and glycoproteins. In some instances α-galactosidase can hydrolyzes ceramide trihexoside, and it can catalyze the hydrolysis of melibiose into galactose and glucose. In some instances the α-galactosidase can be encoded by the GLA gene. The term "β-galactosidase, indicates a hydrolase enzyme that catalyzes the hydrolysis of β-galactosides into monosaccharides. Substrates of different β-galactosidases comprise ganglioside GM1, lactosylceramides, lactose, and various glycoproteins identifiable by a skilled person. In particular, β-galactosidase is an exoglycosidase which hydrolyzes the β-glycosidic bond formed between a galactose and its organic moiety. It may also cleave fucosides and arabinosides but with much lower efficiency.

In embodiments, herein described α-galactosidase and β-galactosidase can be used alone or in combination with other active ingredients for treatment and/or prevention of a GERD in an individual.

The term "individual" or "subject' or "patient" as used herein in the context of treatment includes a single animal and in particular higher animals and in particular vertebrates such as mammals and in particular human beings. In general "individual" in the sense of the present disclosure indicate an animal that has a gastrointestinal (herein also GI) system and that are susceptible to gastric and esophageal ulcerations.

In particular, in some embodiments, the present disclosure relates to pharmaceutical or nutritional compositions containing a combination of the active ingredients alpha-galactosidase and beta-galactosidase alone or in combination with other active ingredients, mixed with at least one nutraceutically and/or pharmaceutically acceptable excipient or carrier.

As used herein a "nutritional composition" indicates a product which depending on its ingredients and the claims with which it is marketed can be identified as dietary supplement, food ingredient, or food. Accordingly, nutritional compositions in the sense of the disclosure range from isolated nutrients, dietary supplements and herbal products, specific diets and processed foods such as cereals, soups, and beverages.

As used herein the wording "pharmaceutical composition" indicates any chemical substance formulated or compounded as single active ingredient or in combination of other pharmacologically active substance, it may be in a separate but packed in a single unit pack as combination product intended for internal, or external or for use in the medical diagnosis, treatment, or prevention of a condition and in particular a disease As used herein, the term "active ingredient" or "AI" indicates the substance in a composition (and in particular in a pharmaceutical or nutritional composition) that is biologically active. In particular, an active ingredient as recited herein indicates a substance that is biologically active with reference to a GERD or other disorder, e.g. a substance suitable for treatment and/or prevention of GERD.

As used herein, the term "pharmaceutically acceptable" includes moieties or compounds that are, within the scope of sound medical judgment, suitable for use in contact with the tissues of humans and lower animals without undue toxicity, irritation, allergic response, and the like, and are commensurate with a reasonable benefit/risk ratio.

The term "excipient" as used herein indicates an inactive substance that can be used any of various media acting usually as solvents, binders or diluents to bulk up formulations that contain active ingredients (thus often referred to as "bulking agents," "fillers," or "diluents"), to allow convenient and accurate dispensation of a drug substance when producing a dosage form. Suitable excipients can include any substance that can be used to bulk up formulations with alpha-galactosidase and/or beta galactosidase to allow for convenient and accurate dosage. In addition to their use in the single-dosage quantity, excipients can be used in the manufacturing process to aid in the handling of alpha-galactosidase and/or beta galactosidase. Depending on the route of administration, and form of medication, different excipients may be used. Exemplary excipients include but are not limited to antiadherents, binders, coatings disintegrants, fillers, flavors (such as sweeteners) and colors, glidants, lubricants, preservatives, sorbents.

The term "carrier" as used herein indicates an inactive substance that serves as mechanisms to improve the delivery and the effectiveness of drugs and can be identified by a skilled person in view of the route of administration and related composition formulation.

In some embodiments, compositions herein described can be administered orally.

In various embodiments, pharmaceutical or nutritional compositions for the prevention and/or treatment of gastroesophageal reflux disease herein described and in particular compositions containing α-galactosidase and β-galactosidase as active ingredients can be formulated by conventional methods.

In some embodiments, dosage forms are solid formulations for oral administration, such as powders, granules, tablets, pills and capsules.

In some embodiments, pharmaceutical or nutritional compositions containing α-galactosidase and β-galactosidase have been surprisingly found to be useful in the prevention and/or treatment of gastroesophageal reflux disease (GERD).

In particular in some embodiments, administration of both alpha- and beta-galactosidase can favor both the digestion of aliments rich of either oligosaccharides or lactose, reducing the rate of TLESRs and the number of acid reflux episodes.

More particularly, in some embodiments, compositions comprising both alpha-galactosidase and beta-galactosidase allow the digestion of food rich of both lactose and oligosaccharides with a resulting beneficial effect to the patients suffering by GERD.

In some embodiments, a composition herein described can provide an improved pharmaceutical or nutritional composition efficacious in the treatment of GERD, possibly providing also an alternative strategy of treatment for patients' non responder to the conventional therapy.

In some embodiments, when compositions herein described are prepared, the active ingredients can be mixed with at least one pharmaceutically acceptable excipient or carrier, such as an inert diluent, a lubricant such as magnesium stearate, an anti-caking agent such silicon dioxide, a preservative, an antioxidant, a disintegrant, a binder, a thickening agent, a buffer, a sweetener such as acesulfame potassium, a flavouring agent, and additional excipient or carrier identifiable by a skilled person.

Further dosage forms can be liquid formulations for oral administration including, for example, emulsions, syrups, elixirs, suspensions and solutions.

The dose of the active ingredients for each patient is determined on the basis of age, body weight, general state of health, gender, diet, condition of the disease treated and/or other factors identifiable by a skilled person.

The quantity of the active ingredients in the composition of the disclosure can range from 75 GalU to 2400 GalU for α-galactosidase, possibly from 300 GalU to 1200 GalU, and in particular amounts to 300 GalU in the form of dosage units, and from 2500 to 12500 LactU for β-galactosidase, possibly from 3500 to 11000 LactU, and in particular amounts to 4500 LactU in the form of dosage units. In some embodiments the β-galactosidase active can be comprised in the composition in amount of 69 mg (65000 LactU/g). In some embodiments the α-galactosidase can be comprised in the composition in an amount of 30 mg (10000 GalU/g).

Additional dosages can be used which provide the individual with a therapeutic effective amount or a prophylactic effective amount in accordance with the related embodiments of the disclosure. In particular, the term "effective amount" of one or more active ingredients refers to a nontoxic but sufficient amount of one or more drugs to provide the desired effect. For example, an "effective amount" associated with the treating and/or preventing (herein also "therapeutically effective amount")

The dosage unit form is usually administered one or more times a day, as required. In some embodiments, the dosage unit of at least one of α-galactosidase and β-galactosidase, possibly both α-galactosidase and β-galactosidase can be administered 3 times a day. In some embodiments, α-galactosidase and β-galactosidase can be given at different times of the day before or after meals according to different schedules as required. In some embodiments, α-galactosidase and β-galactosidase can be given at a same time of the day, before or after meals as required. In some embodiments, an effective amount of α-galactosidase and β-galactosidase can be administered to patients one or more times and in particular three times a day before meals to treat or prevent gastoesophageal reflux disease.

Accordingly, in some embodiments, the effective amount of α-galactosidase administered daily can be from 75 to 2400 GalU, 150 to 4800 GalU or 225 to 7200 GalU. In some embodiments, the effective amount of β-galactosidase administered daily can be from 2500 to 12500 LactU, 5000 to 25000 LactU or 7500 to 37500 LactU.

In some instances, α-Galactosidase has proved to prevent the onset of bloating and flatulence symptoms after intake of Non-digestible Oligosaccharides (NDOs) and/or to reduce the intensity of heartburn and the frequency of regurgitation episodes during repeated administration to patients with gastroesophageal reflux disease.

In some embodiments, a combination of α-galactosidase and β-galactosidase has provided an unexpected symptomatic benefit in some patients, who respond unsatisfactory to conventional therapy based on PPI. There is initial evidence that the combination of the two substances boosts the effects by reducing the frequency and duration of reflux to an extent which is markedly high.

The pharmaceutical or nutritional compositions to which the present disclosure relates can be also added to the existing treatments (e.g. as an "add-on therapy"), leading to a significant improvement in the quality of life of many patients with gastroesophageal reflux disease. The term "add-on therapy" or "combined administration" of one therapeutic agent, or administration of an active ingredient and in particular a therapeutic agent in combination with one or more further active ingredients such as other therapeutic agents in the sense of the present disclosure comprises simultaneous (concurrent) and consecutive administration of the referenced principles performed in any order.

Suitable dosages and timing of administration of the galactosidase, gastric acid inhibitor, particularly a proton pump inhibitor, and other active ingredient, will be identifiable by a skilled person based on the galactosidase, gastric acid inhibitor and other active ingredient selected and the specific GERD treated as will be understood by a skilled person. Similarly specific formulations of the galactosidase, gastric acid inhibitor and other active ingredient can also be identifiable by a skilled person upon reading of the present disclosure based on the galactosidase, gastric acid inhibitor and other active ingredient selected and the specific GERD treated. The term "gastric acid inhibitor" as used herein refers to any compound that would have the effect of reducing the acid content of the stomach.

As will be apparent to one skilled in the art, the useful in vivo dosage to be administered and the particular mode of administration will vary depending upon the age, weight and mammalian species treated, the particular compounds employed, and/or the specific use for which these compounds are employed. The determination of effective dosage levels, that is the dosage levels necessary to achieve the desired result, can be accomplished by one skilled in the art using routine pharmacological methods. Typically, human clinical applications of products are commenced at lower dosage levels, with dosage level being increased until the desired effect and durability of response is achieved. As used herein, "durability of response" includes for example, adequate relief of symptoms after removal of treatment, continuous adequate relief of symptoms after removal of treatment, or response that is greater than or superior to placebo response. The response can be measured, for example using one or more of the methods outlined below, including, for example, a subject's subjective assessment of their symptoms or a healthcare provider's or caretaker's assessment of a subject's symptoms.

As with other pharmaceuticals, it will be understood that the total daily usage of one or more pharmaceutical compositions of the present disclosure will be decided by a patient's attending physician within the scope of sound medical judgment. The specific therapeutically effective or prophylactically effective dose level for any particular patient will depend upon a variety of factors including the disorder being treated and the severity of the disorder; activity of the specific compound employed; the specific composition employed; the age, body weight, general health, sex and diet of the patient; the time administration, route of administration, and rate of excretion of the specific compound employed; the duration of the treatment; drugs used in combination or coincidental with the specific compound employed; and other factors known to those of ordinary skill in the medical arts.

Accordingly, the amount of drug that is "effective" will vary from subject to subject, depending on the age and general condition of the individual, the particular drug or drugs, and the like and an appropriate "therapeutically effective amount" or "prophylactically effective amount" in any individual case can be determined by one skilled in the art.

In some embodiments, compositions and methods herein described have a success rates comparable or higher than conventional approaches when taking into account remission and improvement of symptoms. The examples given below further illustrate the disclosure. In particular, various characteristics of the present disclosure will become more apparent hereinafter from the following detailed disclosure by way of illustration only with reference to an experimental section.

EXAMPLES

The compositions, methods system herein described are further illustrated in the following examples, which are provided by way of illustration and are not intended to be limiting.

Example 1

Formulation

The composition according to the disclosure in the form of a tablet to be swallowed or chewed contains:
69 mg β-galactosidase (65000 LactU/g)
30 mg α-galactosidase (10000 GalU/g)
280 mg sorbitol
22.78 mg flavouring
8 mg crosslinked sodium carboxymethylcellulose
8 mg magnesium stearate
2 mg silicon dioxide
0.22 mg acesulfame potassium Example 2

Formulation

The composition according to the disclosure in the form of a tablet to be swallowed contains:
69 mg β-galactosidase (65000 LactU/g)
30 mg α-galactosidase (10000 GalU/g)
280 mg sorbitol
8 mg crosslinked sodium carboxymethylcellulose
8 mg magnesium stearate
2 mg silicon dioxide
30 mg ginger (*Zingiber officinale*) extract.

Example 3

Clinical Study

The clinical trial was a double blind study, randomized, wherein patients affected by GERD are enrolled. The patients were male or non-pregnant, non-lactating female, between 22 years and 46 years old.

Before the start of the trial two groups of patients have been already treaded with conventional therapy with PPI or anti acid.

The group 1 was treated with pantoprazol from 2011 to 2012.

The group 4 was treated with magaldrate in 2012.

The study was carried out in two days. The first day the patients have received a meal rich in carbohydrates such as oligosaccharides and lactose and the compositions of Example 1 comprising alpha- and beta-galactosidase three times a day before meals. After at least 7 days the patients have received the same meal and the placebo compositions three times a day before meals.

The patients underwent a basal 24-hour esophageal pH-metric recording monitoring the type of refluxes (acid, basic).

The symptoms as heart-burn and regurgitation were also scored by means of a questionnaire wherein the duration and the intensity of symptoms were recorded. The score 1, 2 and 3 are related to the intensity of the symptoms respectively mild, acute and severe.

Table 1 reports the time wherein the pH values were less than 4 in the 24 hours. The values are reported as percentage of time (hours) in respect to 24 hours.

TABLE 1

| | Percentage % Time pH < 4/24 hours | |
|---|---|---|
| Treatment Group | Composition containing α and β galactosidase | Placebo |
| Group 1 | 1.5 | 4.1 |
| Group 2 | 2.1 | 5.9 |
| Group 3 | 2.6 | 5.2 |
| Group 4 | 1.7 | 3.8 |

Table 2 reports the number of reflux episodes during 24 hours.

TABLE 2

| | Number Acid refluxes | | Number Basic refluxes | | Number Total Refluxes | |
|---|---|---|---|---|---|---|
| Treatment Group | Composition containing α and βgalactosidase | Placebo | Composition Alpha and beta galactosidase | Placebo | Composition Alpha and beta galactosidase | Placebo |
| Group 1 | 15 | 20 | 28 | 62 | 43 | 82 |
| Group 2 | 12 | 29 | 10 | 47 | 22 | 76 |
| Group 3 | 14 | 28 | 14 | 37 | 28 | 65 |
| Group 4 | 21 | 46 | 19 | 56 | 40 | 102 |

Table 3 reports the heart-burn and regurgitation scored as a product of intensity (1, 2 or 3) for number of episodes recorded in the 24 hours.

TABLE 3

| Treatment Group | Heart-burn | | Regurgitation | |
|---|---|---|---|---|
| | Composition containing α and β galactosidase | Placebo | Composition containing α and β Galactosidase | Placebo |
| Group 1 | 8 | 36 | 8 | 16 |
| Group 2 | 16 | 58 | 6 | 20 |
| Group 3 | 20 | 44 | 10 | 18 |
| Group 4 | 22 | 72 | 12 | 22 |

During and after the administration of the composition comprising alpha and beta galactosidase the patients have showed a significant reduction of the number of reflux episodes and the percentage of time wherein the values of pH were less than 4 with respect to the placebo. Heart-burn and regurgitation were also reduced in patients assuming alpha and beta galactosidase as compared to the placebo.

Furthermore this clinical trial points out that the group 1 already treated with PPI and the group 4 already treated with anti acid before the treatment with the composition comprising alpha and beta-galactosidase, have showed a significant improvements in the number of reflux episodes and the severity of the reflux symptoms demonstrating that the composition object of the present disclosure is suitable for the non-responders patients to conventional therapy or as alternative strategy therapy for the treatment of GERD.

In summary, in some embodiments a pharmaceutical or nutritional composition is described containing α-galactosidase and β-galactosidase and at least one pharmaceutically acceptable excipient or carrier.

In some embodiments, in the pharmaceutical or nutritional composition the content of α-galactosidase ranges from 75 to 2400 GalU and the content of β-galactosidase ranges from 2500 to 12500 LactU in the form of a dosage unit.

In some embodiments, the pharmaceutical or nutritional composition herein described can be for use in the prevention and/or treatment of a gastroesophageal reflux disease.

In some embodiments a method to treat or prevent a gastroesophageal reflux disease in an individual, is described the method comprising administering to the individual an effective amount of α-galactosidase and β-galactosidase.

In some embodiments, in methods herein described the administering can be performed as add-on therapy wherein the α-galactosidase and β-galactosidase are administered in combination with other active agents in prevention and/or treatment of a GERD.

In some embodiments, a system for treatment or prevention of a gastroesophageal reflux disease in an individual is described, the system comprising α-galactosidase and β-galactosidase for simultaneous combined or sequential use in methods herein described.

In some embodiments, each of the α-galactosidase and β-galactosidase can be comprised in a composition with a suitable excipient or carrier.

In some embodiments of the compositions, methods and systems herein described the α-galactosidase can be administered in an amount from 75 to 2400 GalU and β-galactosidase is administered in an amount from 2500 to 12500 LactU.

In some embodiments, of the compositions, methods and systems herein described administering to the individual can be performed by administering 3 times a day before meals an effective amount of α-galactosidase and β-galactosidase to treat or prevent gastroesophageal reflux disease in an individual.

In some embodiments of the compositions, methods and systems, α-galactosidase can be administered in a daily amount from 75 to 2400 GalU, 150 to 4800 GalU or 225 to 7200 GalU and β-galactosidase is administered in a daily amount from 2500 to 12500 LactU, 5000 to 25000 LactU or 7500 to 37500 LactU.

In some embodiments, of the compositions, methods and systems the effective amount can be 69 mg beta-galactosidase (65000 LactU/g), 30 mg alpha-galactosidase (10000 GalU/g).

The examples set forth above are provided to give those of ordinary skill in the art a complete disclosure and description of how to make and use the embodiments of the compositions, materials, compounds, systems and methods of the disclosure, and are not intended to limit the scope of what the inventors regard as their disclosure. All patents and publications mentioned in the specification are indicative of the levels of skill of those skilled in the art to which the disclosure pertains.

The entire disclosure of each document cited (including patents, patent applications, journal articles, abstracts, laboratory manuals, books, or other disclosures) in the Background, Summary, Detailed Description, and Examples is hereby incorporated herein by reference. All references cited in this disclosure are incorporated by reference to the same extent as if each reference had been incorporated by reference in its entirety individually. However, if any inconsistency arises between a cited reference and the present disclosure, the present disclosure takes precedence.

The terms and expressions which have been employed herein are used as terms of description and not of limitation, and there is no intention in the use of such terms and expressions of excluding any equivalents of the features shown and described or portions thereof, but it is recognized that various modifications are possible within the scope of the disclosure claimed Thus, it should be understood that although the disclosure has been specifically disclosed by embodiments, exemplary embodiments and optional features, modification and variation of the concepts herein disclosed can be resorted to by those skilled in the art, and that such modifications and variations are considered to be within the scope of this disclosure as defined by the appended claims.

It is also to be understood that the terminology used herein is for the purpose of describing particular embodiments only, and is not intended to be limiting. As used in this specification and the appended claims, the singular forms "a," "an," and the include plural referents unless the content clearly dictates otherwise. The term "plurality" includes two or more referents unless the content clearly dictates otherwise. Unless defined otherwise, all technical and scientific terms used herein have the same meaning as commonly understood by one of ordinary skill in the art to which the disclosure pertains.

When a Markush group or other grouping is used herein, all individual members of the group and all combinations and possible subcombinations of the group are intended to be individually included in the disclosure. Every combination of components or materials described or exemplified herein can be used to practice the disclosure, unless otherwise stated. One of ordinary skill in the art will appreciate that methods, device elements, and materials other than those specifically exemplified can be employed in the practice of the disclosure without resort to undue experimentation. All art-known functional equivalents, of any such methods, device elements, and materials are intended to be included in this disclosure. Whenever a range is given in the specification, for example, a temperature range, a frequency range, a time range, or a composition range, all intermediate ranges and all subranges, as well as, all individual values included in the ranges given are intended to be included in the disclosure. Any one or more individual members of a range or group disclosed herein can be excluded from a claim of this disclosure. The disclosure illustratively described herein suitably can be practiced in the absence of any element or elements, limitation or limitations which is not specifically disclosed herein.

A number of embodiments of the disclosure have been described. The specific embodiments provided herein are examples of useful embodiments of the invention and it will be apparent to one skilled in the art that the disclosure can be carried out using a large number of variations of the devices, device components, methods steps set forth in the present description. As will be obvious to one of skill in the art, methods and devices useful for the present methods can include a large number of optional composition and processing elements and steps.

In particular, it will be understood that various modifications can be made without departing from the spirit and scope of the present disclosure. Accordingly, other embodiments are within the scope of the following claims.

The invention claimed is:

1. A method to treat a gastroesophageal reflux disease, the method comprising
    administering to an individual in need thereof an effective amount of α-galactosidase and β-galactosidase.

2. The method according to claim 1, wherein the administering is performed as add-on therapy wherein the α-galactosidase and β-galactosidase are administered in combination with other active agents in prevention and/or treatment of a GERD.

3. The method according to claim 1, wherein α-galactosidase is administered in an amount from 75 to 2400 GalU and β-galactosidase is administered in an amount from 2500 to 12500 LactU.

4. The method according to claim 1, wherein α-galactosidase is administered in a daily amount from 75 to 2400 GalU, or in a daily amount of 150 to 4800 GalU or in a daily amount of 225 to 7200 GalU and β-galactosidase is administered in a daily amount from 2500 to 12500 LactU, or in a daily amount of 5000 to 25000 LactU or in a daily amount of 7500 to 37500 LactU.

* * * * *